United States Patent [19]

Holtkamp

[11] Patent Number: Plant 5,252

[45] Date of Patent: Jul. 3, 1984

[54] AFRICAN VIOLET PLANT NAMED IMPROVED EVELYN

[75] Inventor: Reinhold Holtkamp, Isselburg, Fed. Rep. of Germany

[73] Assignee: Gessellschaftsvertrag uber die Erfindergemeinschaft "Optimara", Rees Haffen, Fed. Rep. of Germany

[21] Appl. No.: 424,360

[22] Filed: Sep. 27, 1982

[51] Int. Cl.[3] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Koch

[57] ABSTRACT

An African violet named Improved Evelyn characterized by its vigorous growth habit; upright flower stems which are generally centrally positioned; large deep violet blue single flowers; floriferous flowering habit with 7–10 flowers being produced per stem, and by its medium green leaves which provide a good contrast to the deep violet color.

1 Drawing Figure

The present invention comprises a new and distinct cultivar of African violet plant, botanically known as *Saintpaulia ionantha,* and hereinafter referred to by the cultivar name Improved Evelyn.

The new cultivar was discovered by me in Isselburg, Germany in March 1981 in a cultivated area containing plants of parent cultivar Evelyn, disclosed in U.S. Plant Pat. No. 4,154, of Hermann Holtkamp Sr. Subsequently reselection and asexual reproduction of the new cultivar by leaf cuttings, as performed by me at Isselburg, West Germany has demonstrated that the combination of characteristics as herein disclosed for the new cultivar are firmly fixed and are retained through successive generations of asexual reproduction.

Improved Evelyn has not been observed under all possible environmental conditions. The phenotype may vary significantly with variations in environment such as temperature, light intensity and day length. The following observations, measurements and values describe the new cultivar as grown in Isselburg, West Germany, and Nashville, Tennessee, under greenhouse conditions which closely approximate those generally used in commercial practice.

The following traits have been repeatedly observed and are determined to be basic characteristics of Improved Evelyn, which in combination distinguish the new cultivar from both its parent and other African violet cultivars known in the industry:

1. Vigorous growth habit.
2. Strong and upright flower stems, which appear primarily at the center of the plant.
3. Large single flowers which are deep violet blue in color, significantly deeper in color and tone from the flowers of the parent cultivar Evelyn.
4. Profuse flowering habit, with 7–10 flowers being produced per stem, with the flowers being very long lasting and non-dropping.
5. The medium green leaves, which are comparable and essential characteristics to the leaves of the parent cultivar, provide a pleasing contrast to the deep violet blue flower color, particularly in view of the tight, profuse centrally located bouquet positioned well above the leaves.

The accompanying photographic drawings shows a typical specimen plant of the new cultivar. The colors appearing in the photograph are as true as possible with color illustrations of this type.

In the following description, color references are made to The Royal Horticultural Society Colour Chart (HCC) issued by Wilson Colour Ltd., except where general colors of ordinary significance are referred to. Color values were taken at approximately 10–11 A.M. under natural light conditions at Nashville, Tenn.

Botanical classification: *Saintpaulia ionantha,* Ramat. cv. Improved Evelyn.

Parentage: Sport of Evelyn, disclosed in U.S. Plant Pat. No. 4,154.

Propagation: The new cultivar holds its distinguishing characteristics through successive propagations by leaf cuttings and by division of shoots.

Plant: Approximately 10 cm. tall when grown in pots, and approximately 20–30 cm. in diameter when fully grown. Growth is somewhat more compact in cooler environments.

Leaves:

*General form.*—Round.
*Diameter.*—5–6 cm.
*Texture.*—Leather-like.
*Aspect.*—Shiny.
*Veins.*—Well pronounced.
*Color (upperside)*—Spinach green 960.
*Color (underside).*—Willow green 00862/3.
*Petiole.*—Brownish green.

Flowers:

*Buds.*—7–10 And more; bell-shaped.
*Sepals.*—5; Spear-shaped. Color: Greenish brown. Calyx: Funnel-shaped. Aspect; Hairy. Peduncle: Greenish brown, relatively short.

Individual flowers:

*Size.*—Approximately 3–3.5 cm. in one direction and 3.5–4 cm. in its longer direction.
*Color.*—General tonality: Deep violet blue; color intensifies somewhat in color environments. Upperside: Aconite violet 937/3. Underside: Campanula violet 37/1.
*Borne.*—Upright on strong flower stems.
*Shape.*—Normal violet shaped; single.
*Corolla.*—A tight bouquet positioned centrally above the leaves.
*Flowering time.*—9–11 weeks after potting.

*Reproductive organs.*—Stamens: 2; compound of 4 cells. Filaments: Styles: Purple; light green base. Pollen color: Canary yellow HCC II #2.

*Roots.*—Well developed white when young and active; later brownish.

*Disease resistance.*—No disease problems noted to date.

General observations: Improved Evelyn is a vigorous grower with large deep violet blue single flowers on strong flower stems, which are upright out of the center of the plant. The medium green leaves provide a good contrast to the flower color.

I claim:

1. A new and distinct cultivar of African violet known by the cultivar name Improved Evelyn, as described and illustrated, and particularly characterized by its vigorous growth habit; upright flower stems which are generally centrally positioned; large deep violet blue single flowers; floriferous flowering habit, with 7–10 flowers being produced per stem, and by its medium green leaves which provide a good contrast to the deep violet color.

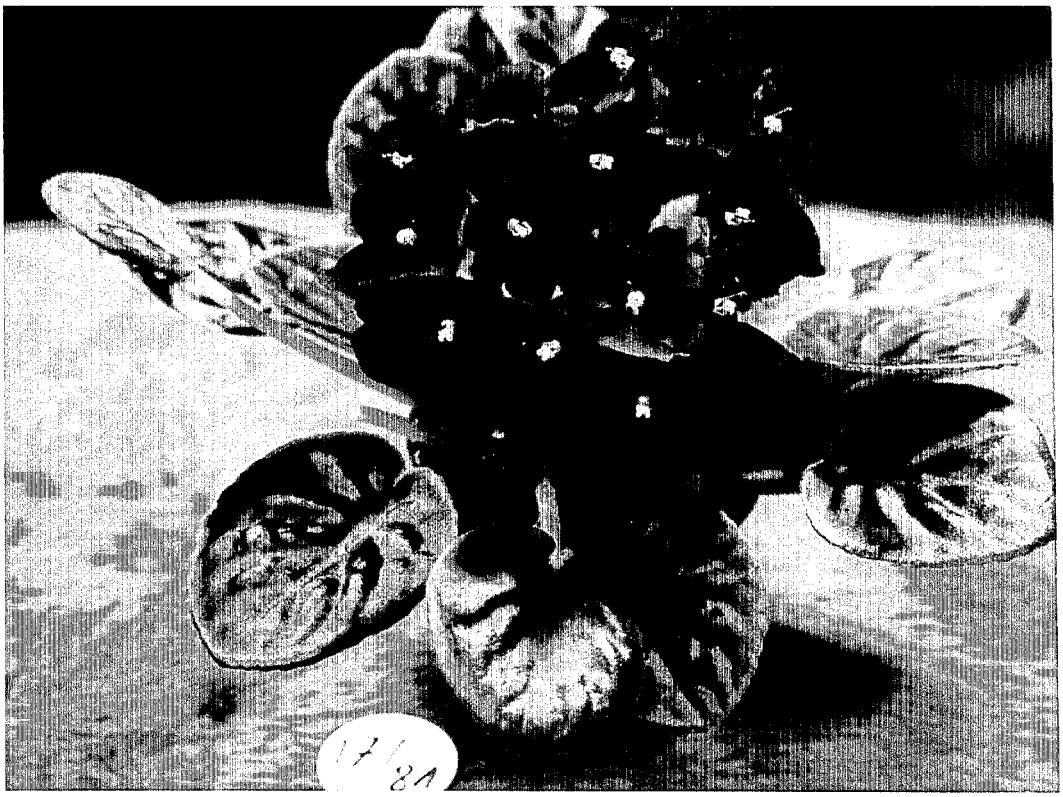

* * * * *